United States Patent [19]
Linnebjerg

[11] Patent Number: 5,928,202
[45] Date of Patent: Jul. 27, 1999

[54] PRELOADABLE SYRINGE FOR AUTOMATED DISPENSING DEVICE

[75] Inventor: Steven Linnebjerg, Skaevinge, Denmark

[73] Assignee: Bristol-Myers Sauibb Company, New York, N.Y.

[21] Appl. No.: 09/178,104

[22] Filed: Oct. 23, 1998

Related U.S. Application Data

[60] Provisional application No. 60/063,034, Oct. 23, 1997.

[51] Int. Cl.⁶ .................................................. A61M 5/315
[52] U.S. Cl. ............................................. 604/228; 604/218
[58] Field of Search .................................. 604/228, 218, 604/232, 187

[56] References Cited

U.S. PATENT DOCUMENTS

| | | | |
|---|---|---|---|
| 3,045,674 | 7/1962 | Goldberg | 604/228 |
| 4,252,118 | 2/1981 | Richard et al. | 604/218 |
| 4,869,720 | 9/1989 | Chernack | 604/228 |
| 5,084,017 | 1/1992 | Maffetone | 604/228 X |
| 5,181,912 | 1/1993 | Hammett | 604/228 X |
| 5,222,942 | 6/1993 | Bader | 604/218 X |

*Primary Examiner*—John D. Yasko
*Attorney, Agent, or Firm*—Stuart E. Krieger

[57] ABSTRACT

The hollow cylindrical syringe body has a channel of uniform diameter. A fluid port is situated at one end. The other end defines a funnel-like opening with a diameter greater than that of the channel. A piston is moved along the channel by the end of a push rod which is received through the channel opening. A ball on the push rod lodges in a socket in the piston as the rod pushes the piston toward the port. The socket is formed of resilient fingers which are held by the channel wall in position to retain the ball in the socket, such that the piston can be moved along the channel to load the syringe. When the socket aligns with the funnel-like opening of the channel, the socket fingers spread apart to release the ball from the socket, permitting the push rod to be removed from the loaded syringe.

27 Claims, 3 Drawing Sheets

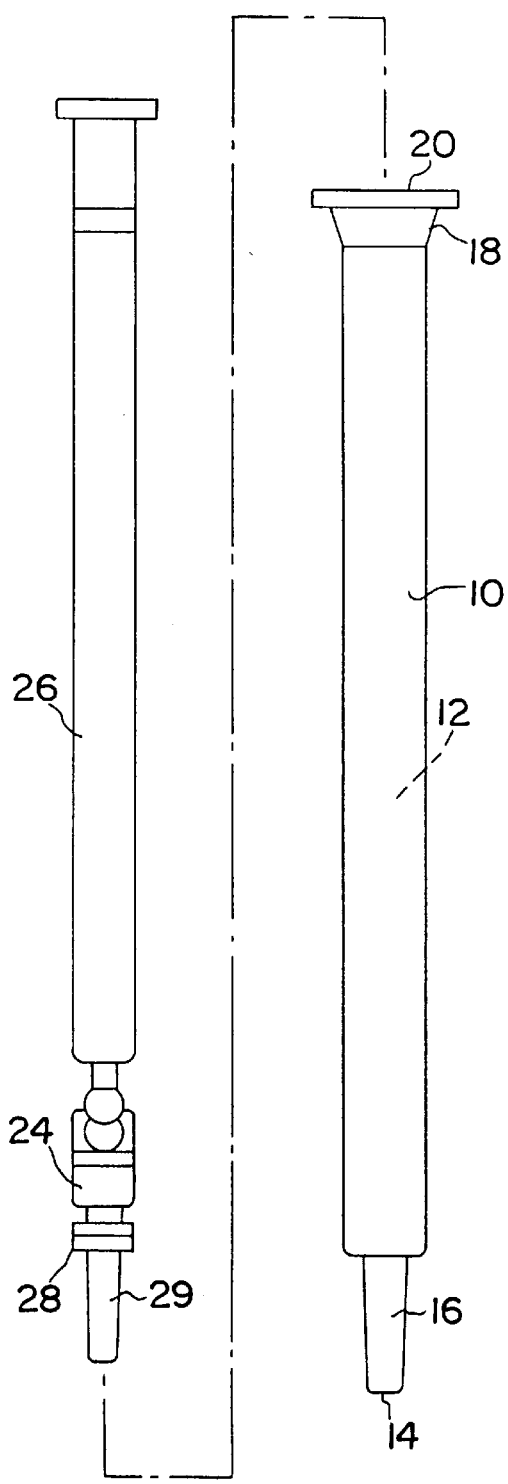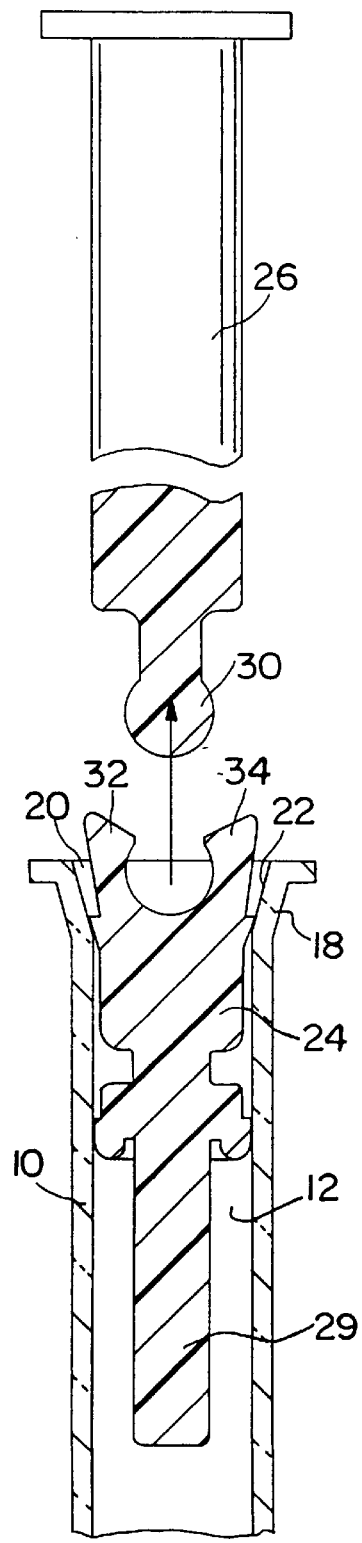
FIG. 1
FIG. 4

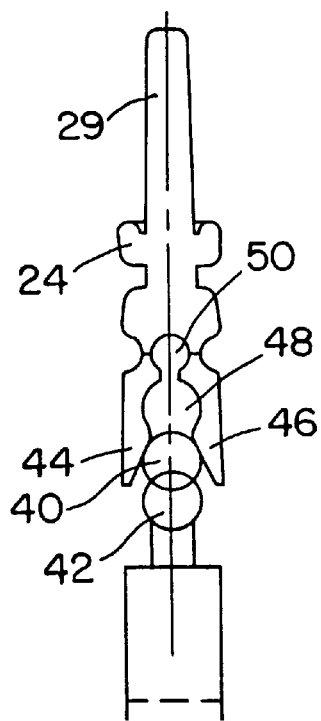
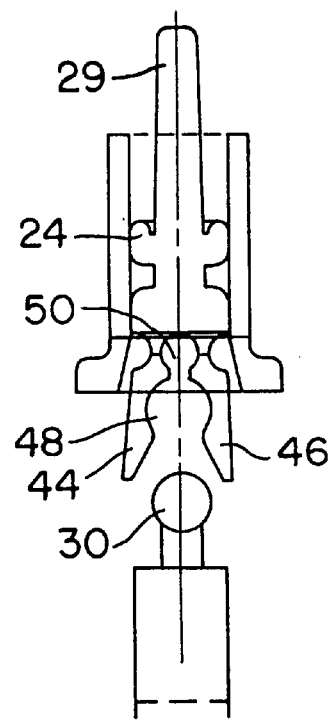
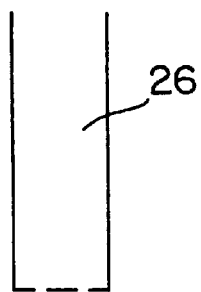
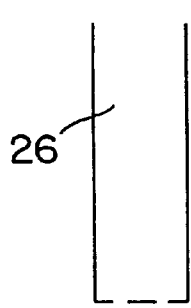
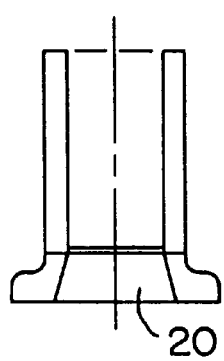
FIG. 5
FIG. 6

PRELOADABLE SYRINGE FOR AUTOMATED DISPENSING DEVICE

This application claims benefit of Provisional Application No. 60/063,034 filed Oct. 23, 1997.

The present invention relates to syringes and more particularly to preloadable syringes designed for use with automated dispensing devices.

Many devices used in the medical field and in research include computer controlled automated devices for delivering measured doses of one or more liquids. For example, infusion pumps deliver precise amounts of one or more medicines to patients intravenously.

The liquids to be dispensed are provided to the device in preloaded syringes. The syringes are retained in recesses in the device. The device has a part which acts as a push rod to push the piston associated with each syringe at a controlled rate to dispense the fluids as required.

The present invention relates to a syringe designed for use with such an automated dispensing device. In particular, it is designed for use with a device of this type which utilizes a push rod adapted to automatically engage the piston of a preloaded syringe to permit the liquid in the syringe to be dispensed and thereafter to automatically disengage the piston, as the rod is withdrawn from the syringe body. This structure permits the syringe to be used repeatedly, each time being preloaded by an operator using a similar, but separate push rod.

Many syringe structures have been devised where the actuating rod is separable from the piston following expulsion of the contents of the syringe, that is, when the piston is situated adjacent the fluid port end of the syringe body. This type of structure is usually designed to prevent reuse of the syringe.

The present invention differs in that the push rod is releaseable from the piston only when the piston is at the end of the syringe body remote from the fluid port. In other words, the push rod is released from the piston after the syringe is loaded, instead of after the contents of the syringe have been expelled.

For example, U.S. Pat. No. 4,391,272 to Staempfli discloses a disposable syringe in which rearward return of the piston is prevented by the interaction of detents on the piston and a groove in the inner wall of the piston barrel. Engagement of the detents with the groove prevent the rearward movement of the piston, allowing the actuating rod to be pulled therefrom. In one embodiment, the end of the rod is provided with a bulbous portion fitting into a corresponding socket in the piston.

U.S. Pat. No. 4,731,068 to Hesse discloses a non-reloadable syringe provided with a plunger unit which is permitted to be withdrawn a single time for loading the syringe but cannot be redrawn following discharge of the contents. In one embodiment, a ball end of the actuating rod engages a socket in the piston such that the socket is maintained in a closed position about the ball by a collar member. As the piston is withdrawn during loading, the collar member is drawn rearwardly with the piston. Upon expulsion of the loaded contents, the collar member remains at the rear end of the barrel, thus releasing the walls of the socket whereby the ball end of the rod is released.

U.S. Pat. No. 4,887,999 to Alles discloses a single use hypodermic syringe employing a ratchet structure within the syringe barrel to ensure single use of the syringe. The plunger rod connects to the piston by a ball and socket which provides a frangible connection that breaks if an attempt is made to overcome the ratchet following dispensing of the syringe contents.

U.S. Pat. No. 4,931,040 to Haber discloses a safety syringe having a retractable needle structure whereby the piston engages the needle so as to draw it back into the syringe barrel following dispensing of the contents. The actuator rod attaches to the piston by means of one or more sets of jaws which grab the rear end of the piston and are held in place by the confinement of the syringe barrel. In an alternative embodiment, a lug on the end of the rod is held in a spreadable socket in the end of the piston which socket is held closed about the lug by means of the barrel wall but when the piston is withdrawn to the end of the barrel is allowed to spread and release the rod.

U.S. Pat. No. 5,149,323 to Colonna discloses a self destructing syringe wherein the forward end of the actuating rod is held in engagement with a socket receiver in the rear of the piston during an initial loading of the syringe by means of a locking sleeve. The sleeve frictionally engages the inner wall of the syringe so as to be wedged in place when the rod is pushed forward thus releasing the walls of the socket whereby the rod will be removed from the piston if an attempt is made to reuse the syringe.

U.S. Pat. No. 5,269,760 to Bina discloses a non-resuable syringe having a releasable ball and socket joint between the actuator rod and the piston. Attempted removal of the rod and piston for reuse of the syringe results in the separation of the joint so that the piston remains at the bottom of the syringe barrel. In addition, the patent discloses locking means between the needle shield and the end of the barrel whereby attempted removal of the shield after use fractures the barrel adjacent to the ball and socket joint also resulting in the separation of the rod and the piston.

In general, the present invention utilizes a piston with a ball receiving socket defined by resilient fingers. The socket fingers are held by the channel wall of the syringe body in a position where the push rod ball is retained in the socket. This permits movement of the piston and the loading of the syringe. Once the syringe is loaded and the piston is located at the end of the syringe body, the ball is released, permitting the rod to be removed, because the diameter of the funnel-like channel end is larger than that of the channel and the socket fingers are no longer prevented from separating to enable the ball to be removed.

It is therefore, a prime object of the present invention to provide a preloadable syringe for use with an automated delivery device which incorporates a piston which automatically releases the push rod when the piston is situated at the end of the syringe remote from the fluid port.

It is another object of the present invention to provide a preloadable syringe for use with an automated delivery device which includes resilient parts on the piston which are held by the wall of the syringe body channel to retain the connection between the push rod and the piston.

It is another object of the present invention to provide a preloadable syringe for use with an automated delivery device which is reuseable.

In accordance with the present invention, a syringe is provided including a hollow cylindrical body with a channel defined by a wall with a substantially uniform inner diameter. A fluid port is situated at one end of the body. The second body end has an opening with a diameter greater than the diameter of the channel. A piston is situated in the channel. A push rod extends through opening in the second body end and into the channel to engage and move the piston along the channel. Means are provided for conditionally engaging the rod and the piston. The engaging means normally cooperates with the channel wall to maintain the engagement between the rod and piston. However, when the piston is aligned with the second body end, the engaging means no longer cooperates with the channel wall to retain the rod. The rod then disengages from the piston to permit removal of the rod from the syringe.

The engaging means includes a first part asociated with the rod and a second part associated with the piston. The second part includes a first part receiving recess. The first part receiving recess includes resilient means. The resilient means are caused by the channel wall to retain the first part when the piston is within the channel, but when the second part is aligned with the second body end, the resilient means separate to release the first part from the second part.

The resilient means, in its separated state, has an outer diameter larger than the inner diameter of the channel wall. The resilient means, in its non-separated state, has an outer diameter substantially equal to the inner diameter of the channel wall.

The opening in the second body end has a gradually increasing diameter. The interior wall of the second body end is substantially conical.

In the preferred embodiment, the engaging means includes a ball associated with the rod and a socket associated with the piston. The socket includes a ball receiving recess. The ball receiving recess includes resilient members. The members are retained in the non-separated state by the channel wall, when the piston is in the channel. However, when the socket is aligned with the second body end, the members separate to release the ball from said socket.

The rod and the piston are preferably initially connected. Preferably, the rod and piston are initially integral. Breakable means are provided to initially connect the rod and the piston.

The second part preferably includes a recess adjacent the first part receiving means. More particularly, the socket includes a recess adjacent the ball receiving recess.

The resilient means comprises first and second resilient fingers each defining a portion of the first part receiving recess. Each of the fingers has an interior surface substantially corresponding to the shape of the outer surface of the first part. Preferably, the first and second resilient fingers define portions of the ball receiving recess. Each of the fingers has an interior surface with an arcuate shape.

The first part receiving means further comprises means, cooperating with the first part receiving means, to receive the first part, when the piston is within the channel.

The ball receiving recess includes means, cooperating with the ball, to cause the resilient fingers to separate such that the ball receiving recess can receive the ball, when the piston is within said channel.

To these and such other objects which may hereinafter appear, the present invention relates to a preloadable syringe for use in an automated delivery device as set forth in detail in the following specification and recited in the annexed claims, taken together with the accompanying drawings, wherein like numerals refer to like part and in which:

FIG. 1 is an exploded plan view of a first preferred embodiment of the invention;

FIG. 4 is a view similar to FIG. 2 but, showing the push rod after disengagement from the piston;

FIG. 5 is a plan view of a second preferred embodiment of the invention; and

FIG. 6 is a plan view of a third preferred embodiment of the invention.

Figure 2:
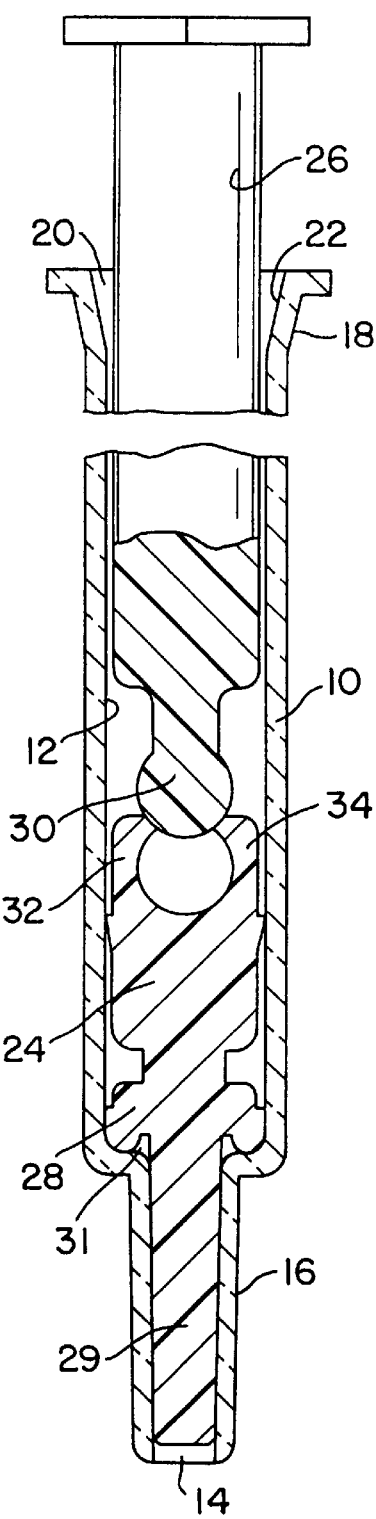
FIG. 2 is an enlarged cross-section view showing the push rod and socket prior to engagement.

As seen in the figures, the syringe of the present invention includes a hollow cylindrical syringe body 10 composed of plastic on glass. Body 10 has an internal channel 12 with a substantially uniform inner diameter.

The fluid port 14 at one end of the body 10 is defined by a decreased diameter section 16. The other end of body 10 is defined by an outwardly flared end section 18 which has a funnel-like opening 20 defined by a conical wall 22. Opening 20 has a diameter which is larger than the diameter of channel 12 and gradually increases in size.

The invention also includes a piston 24 adapted to be received in and moved along channel 12 by a push rod 26. When in use, the end of push rod 26 extends outwardly from end section 18 so as to be accessible from the exterior of the syringe. Piston 24 has an elongated forward section 29 adapted to be received in section 16 of the syringe to insure that the contents of the syringe have been completely expelled.

Figure 3:
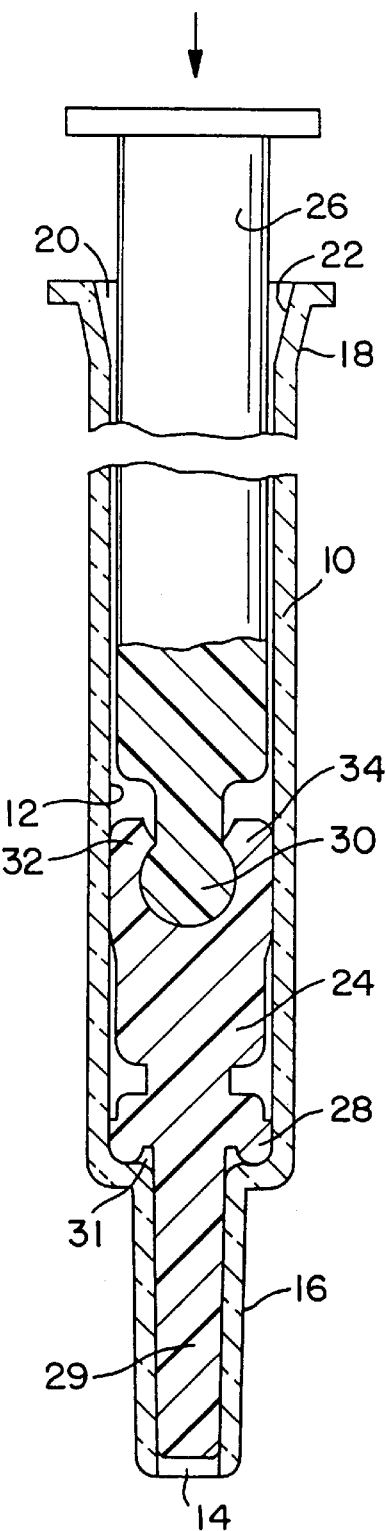
FIG. 3 is a view similar to FIG. 2 but showing the push rod and socket after engagement.

Initially, piston 24 and push rod 26 are preferably connected together as a unit by adhesive or the like or are integral, as seen in FIG. 1. The piston/rod unit is inserted through opening 20 into the channel 12 and moved toward port 14. When the collar 28 of the piston 24 abuts end 31 of body 10, as seen in FIG. 2, forward movement of the piston ceases. Further movement of rod 26 in that direction causes ball 30 on the foward end of rod 26 to cam resilient fingers 32, 34 apart such that ball 30 is received within the recess 36 defined between fingers 32, 34, see FIG. 3. This is possible because fingers 32, 34, which define a spherical socket due to their arcuate inner surfaces, are composed of resilient plastic material. A slight clearance between the exterior surfaces of the fingers and the interior surface of the channel wall is present to permit this movement, see FIG. 2.

The wall which defines channel 12 bears on the exterior surface of fingers 32, 34 when the ball 30 is received therein, holding the fingers together to retain the ball and thus maintain the engagement between the piston and push rod. This permits the piston to be moved along the channel to draw liquid into the syringe so as to load the syringe as the rod is withdrawn.

When piston 24 is moved such that fingers 32, 34 align with wall 22 of the end section 18, they are no longer held together by the channel wall. The fingers are then free to spread apart, expanding the mouth of the socket to release ball 30 (see FIG. 4) such that rod 26 separates from piston 24.

Thereafter, the preloaded syringe (without rod 26) is placed in the automated dispensing device. The device has its own push rod with a ball identical to ball 30. The push rod of the device is inserted into opening 20 and moved forward to engage piston 24. It can then push piston 24 along channel 12 to expel the contents of the syringe, as needed. The rod is then moved in the opposite direction, withdrawing the piston until fingers 32, 34 align with wall 22 of end 18, at which point the ball on the push rod is released from the socket as fingers 32, 34 spread apart. The syringe can then be cleaned and reused, as required.

As seen in FIG. 5, ball 30 can be replaced by tandam spheres 40, 42 and fingers 32, 34 can be replaced by fingers 44, 46 which define a socket of two portions, a larger portion 48 and a small portion SO the latter of which facilitates opening of the fingers. As shown in FIG. 6, fingers 44, 46 can be utilized with a single ball such as ball 30, as well.

It will now be appreciated that the present invention relates to a preloadable syringe for use with an automated delivery device in which the walls of the syringe body channel hold the resilient members of the socket together to retain the ball and thus maintain engagement between the push rod and the piston to permit loading the syringe. As the rod is withdrawn, the piston aligns with the funnel-like opening in the end section of the syringe body, permitting the socket members to separate and release the ball, so as to disengage the rod from the piston.

While only a limited number of preferred embodiments have been disclosed herein for purposes of illustration, it is obvious that many variations and modifications could be made thereto. It is intended to cover all of these variations and modifications which fall within the scope of the invention, as defined by the following claims:

I claim:

1. A syringe comprising a hollow cylindrical body with a channel defined by a wall with a substantially uniform inner diameter, a fluid port at one end of said body and a second body end, said second body end comprising an opening with a diameter greater than said diameter of said channel, a piston adapted to received in and moved along said channel, a push rod adapted to extend through said second body end opening and into said channel to move said piston along said channel, means for conditionally engaging said rod and said piston, said engaging means normally cooperating with said channel wall to maintain said engagement, but when aligned with said second body end opening such that it can no longer cooperate with said channel wall, disengaging said rod from said piston to permit removal of said rod from said syringe.

2. The syringe of claim 1 wherein said engaging means comprises a first part associated with said rod and a second part associated with said piston, said second part comprising a first part receiving recess.

3. The syringe of claim 2 wherein said first part receiving recess comprises resilient means.

4. The syringe of claim 3 wherein said resilient means is caused by said channel wall to retain said first part when said piston is within said channel, but when said second part is aligned with said second body end, said resilient means spreads to release said first part from said second part.

5. The syringe of claim 3 wherein said resilient means, in its spread state, has an outer diameter larger than said inner diameter of said channel wall.

6. The syringe of claim 3 wherein said resilient means, in its non-spread state, has an outer diameter substantially equal to the inner diameter of said channel wall.

7. The syringe of claim 1 wherein said second body end opening has a gradually increasing diameter.

8. The syringe of claim 1 wherein said second body end opening is defined by a substantially conical wall.

9. The syringe of claim 1 wherein said engaging means comprises a ball associated with said rod and a socket associated with said piston, said socket comprising a ball receiving recess.

10. The syringe of claim 9 wherein said ball receiving recess comprises resilient means.

11. The syringe of claim 10 wherein said resilient means is retained in the non-spread state by said channel wall when said piston is in said channel, but when said socket is aligned with said second body end opening, said resilient means spreads to release said ball from said socket.

12. The syringe of claim 10 wherein said resilient means, in its spread state, has an outer diameter larger than said inner diameter of said channel wall.

13. The syringe of claim 10 wherein said resilient means, in its non-spread state, has an outer diameter substantially equal to the inner diameter of said channel wall.

14. The syringe of claim 9 wherein said second body end opening has a gradually increasing diameter.

15. The syringe of claim 9 wherein said second body end opening is defined by a substantially conical wall.

16. The syringe of claim 1 wherein said rod and said piston are initially connected.

17. The syringe of claim 1 wherein said rod and said piston are initially integral.

18. The syringe of claim 1 further comprising breakable means initially connecting said rod and said piston.

19. The syringe of claim 2 wherein said second part comprises a recess adjacent said first part receiving means.

20. The syringe of claim 9 wherein said socket comprises a recess adjacent said ball receiving recess.

21. The syringe of claim 2 wherein said resilient means is composed of resilient material.

22. The syringe of claim 2 wherein said resilient means comprises first and second resilient members defining said first part receiving recess.

23. The syringe of claim 22 wherein each of said members has an interior surface substantially corresponding to the shape of the outer surface of said first part.

24. The syringe of claim 10 wherein said resilient means comprises first and second resilient members defining said ball receiving recess.

25. The syringe of claim 24 wherein each of said members has an interior surface with an arcuate shape.

26. The syringe of claim 3 wherein said first part receiving means further comprises means, cooperating with said first part, to cause said first part receiving means to receive said first part, when said piston is within said channel.

27. The syringe of claim 10 wherein said ball receiving recess further comprises means, cooperating with said ball, to cause said socket to receive said ball, when said piston is within said channel.

* * * * *